United States Patent [19]

Martin et al.

[11] 3,944,562

[45] Mar. 16, 1976

[54] αS, 4S, 5R α-AMINO-3-CHLORO-4-HYDROXY-2-ISOXAZOLINE-5-ACETIC ACID

[75] Inventors: David G. Martin; Ladislav J. Hanka, both of Kalamazoo, Mich.

[73] Assignee: The Upjohn Company, Kalamazoo, Mich.

[22] Filed: Apr. 17, 1974

[21] Appl. No.: 461,635

[52] U.S. Cl............. 260/307 F; 195/29; 260/239.9; 260/999
[51] Int. Cl.². ........................................ C07D 261/04
[58] Field of Search................................. 260/307 F

[56] References Cited
UNITED STATES PATENTS
3,856,807  12/1974  Hanka et al.................... 260/307 F

OTHER PUBLICATIONS

Hanka et al. – C.A. 79, 100631f, (1973) – Abstract of Cancer Chemother. Rep., Part I (1973), 57(2), 141–147.
Martin et al. – Tetrahedron Lett. 1973, (27), 2549–2552.

*Primary Examiner*—Raymond V. Rush
*Attorney, Agent, or Firm*—Roman Saliwanchik

[57] ABSTRACT

Antibiotic U-43,795, producible by culturing *Streptomyces sviceus* in an aqueous nutrient medium has the following structure

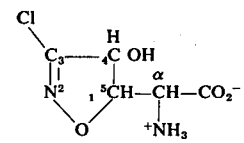

The absolute configuration of U-43,795 was determined to be αS, 4S, 5R α-amino-3-chloro-4-hydroxy-2-isoxazoline-5-acetic acid. It is an amphoteric compound and can exist in different ionic forms according to the pH of the environment. At low pH, U-43,795 exists in the acid-addition salt form, at a higher pH in a zwitterion form, and at still higher pH in a metal salt form. U-43,795 inhibits the growth of *Bacillus subtilis* and *Sarcina lutea*, and can be used to inhibit such microorganisms in various environments.

8 Claims, No Drawings

αS, 4S, 5R α-AMINO-3-CHLORO-4-HYDROXY-2-ISOXAZOLINE-5-ACETIC ACID

The invention described herein was made in the course of, or under Contracts PH43-NCl-68-1023 and NIH-NCl-C-73-3707 with the National Cancer Institute, National Institutes of Health, Bethseda, Md. 20014.

BACKGROUND OF THE INVENTION

Antibiotic AT-125 (U-42,126), producible by culturing Streptomyces sviceus in an aqueous nutrient medium has the following structure:

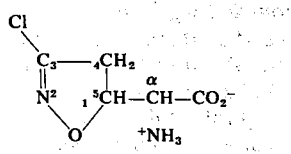

The absolute configuration of AT-125 was determined to be (αS, 5S)-α-amino-3-chloro-2-isoxazoline-5-acetic acid. Like U-43,795, it is also an amphoteric compound and can exist in different ionic forms according to the pH of the environment. At low pH, AT-125 exists in the acid-addition salt form, at a higher pH, in a zwitterion form, and at still higher pH in a metal salt form.

Also, AT-125 inhibits the growth of *Bacillus subtilis*, *Saccharomyces pastorianus*, *Penicillium oxalicum*, *Candida albicans*, *Saccharomyces cerevisiae* and *Escherichia coli*, and can be used to inhibit such microorganisms in various environments.

BRIEF SUMMARY OF THE INVENTION

U-43,795 is an amphoteric antibiotic which is producible concurrently with antibiotic AT-125 by culturing an AT-125-producing actinomycete in an aqueous nutrient medium. U-43,795 has the property of adversely affecting the growth of Gram-positive bacteria, for example, *Bacillus subtilis* and *Sarcina lutea*. It also has marginal activity against *Salmonella gallinarum* and *Bacillus cereus*.

Accordingly, the novel antibiotic of the subject invention can be used alone or in combination with other antimicrobial agents to prevent the growth of, or reduce the number of bacteria, as disclosed above, in various environments. For example, it can be used for treating breeding places of silkworms, to prevent or minimize infections which are well known to be caused by *Bacillus subtilis*.

DETAILED DESCRIPTION

Characterization of U-43,795

The structure of U-43,795, consistent with determined spectral and analytical data is

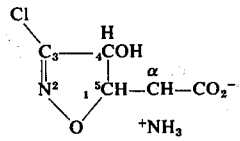

and its ion and zwitterion forms.

The NMR spectrum of a saturated solution of U-43,795 in $D_2O$ was determined on a Varian XL-100-15 spectrometer. The 100 MHz spectrum was not first order and clearly indicated the presence of three nonexchangeable protons. The methine proton on C-4 was seen as an apparent doublet at 5.34 δ with line separation of 8.2 Hz. The neighboring proton on C-5 was seen as an apparent doublet of doublets centered at 5.19 δ with line separations of 3.4 Hz and 8.2 Hz. The signal for the amino acid methine was an apparent doublet at 4.43 δ with line separation of 3.4 Hz.

The IR spectrum of a Nujol mull of U-43,795 partial hydrate was determined on a Perkin Elmer 421 spectrophotometer. Peaks (except Nujol) were found at 3620, 3140, 2710, 2620, 1660, 1640 sh, 1610 sh, 1585, 1525, 1385, 1325, 1310, 1270, 1255, 1180, 1135, 1110, 1075, 980, 915, 900, 865, 805, and 705 $cm^{-1}$ (sh = shoulder).

Circular Dichroism

U-43,795 in water exhibits $[\Theta]_{223}^{max} + 60,000$ and $[\Theta]_{202}^{max} - 47,000$.

TLC

Chromatographing U-43,795 on a silica gel precoated plate (Quanta gram) shows a single zone after spraying the plate with ninhydrin solution. A Rf. of 0.55 is obtained by developing the plate with tetrahydrofuran:acetone:water in the ratio of 50:30:20.

The chemical structure of U-43,795 in the crystalline form was established rigorously by X-ray diffraction. Crystalline U-43,795 can be named chemically as αS, 4S, 5R α-amino-3-chloro-4-hydroxy-2-isoxazoline-5-acetic acid.

Molecular Weight:

Rigorous X-ray structure established a hydrate of U-43,795 as $C_5H_7ClN_2O_4 \cdot H_2O$ or molecular weight as 212.59.

Solubilities:

Soluble in $H_2O$ and slightly soluble in methanol. Relatively insoluble in ethyl acetate, ether, benzene and chloroform.

Antimicrobial Properties of U-43,795

The following results were obtained with a standard disc plate assay using 13 mm. paper discs and a concentration of 3 mg./ml. of U-43,795.

| Microorganism | Zone of Inhibition (mm) around a 13 mm. Paper Disc |
|---|---|
| *Bacillus cereus* | trace |
| *Bacillus subtilis* (in synthetic agar) | 48 |
| *Bacillus subtilis* (in nutrient agar) | 0 |
| *Lactobacillus casei* | 0 |
| *Sarcina lutea* | 23 |
| *Staphylococcus aureus* | 0 |
| *Mycobacterium avium* | 0 |

-Continued

| Microorganism | Zone of Inhibition (mm) around a 13 mm. Paper Disc |
|---|---|
| *Escherichia coli* (in nutrient agar) | 0 |
| *Escherichia coli* (in synthetic agar) | 0 |
| *Salmonella schottmuelleri* | 0 |
| *Salmonella gallinarum* | 25 hazy |
| *Proteus vulgaris* | 0 |
| *Klebsiella pneumoniae* | 0 |
| *Saccharomyces pastorianus* | 0 |
| *Penicillium oxalicum* | 0 |
| *Saccharomyces cerevisiae* | trace |
| *Streptococcus faecalis* | 38 very hazy |
| *Pseudomonas fluorescens* | 0 |
| *Glomerella cingulata* | trace |

THE MICROORGANISM

The actinomycete used according to this invention for the production of U-43,795 is *Streptomyces sviceus* One of its strain characteristics is the production of antibiotic AT-125 and antibiotic U-43,795

A sub-culture of the living microorganism was deposited and can be obtained from the permanent collection of the Northern Utilization and Research Division, Agricultural Research Services, U.S. Department of Agriculture, Peoria, Ill. Its accession number in this repository is NRRL 5439.

The taxonomy of *Streptomyces sviceus*, as determined by Alma Dietz of the Upjohn Research Laboratory, is published in Volume 3 of Antimicrobial Agents and Chemotherapy, March 1973, at pages 425–431. Said publication is incorporated herein by reference thereto.

Fermentation and Recovery of Antibiotic U-43,795

The new compound of the invention is produced when the elaborating organism is grown in an aqueous nutrient medium under submerged aerobic conditions. It is to be understood also that for the preparation of limited amounts, surface cultures and bottles can be employed. The organism is grown in a nutrient medium containing a carbon source, and an assimilable nitrogen compound or proteinaceous material. Preferred carbon sources include glucose, brown sugar, sucrose, glycerol, starch, cornstarch, lactose, dextrin, molasses, and the like. Preferred nitrogen sources include corn steep liquor, yeast, autolyzed brewer's yeast with milk solids, soybean meal, cottonseed meal, cornmeal, milk solids, pancreatic digest of casein, distillers' solids, animal peptone liquors, meat and bone scraps, and the like. Combinations of these carbon and nitrogen sources can be used advantageously. Trace metals, for example, zinc, magnesium, manganese, cobalt, iron and the like need not be added to the fermentation medium since tap water and unpurified ingredients are used as medium components.

Production of the compound of the invention can be effected at any temperature conducive to satisfactory growth of the microorganism, for example between about 18° and 40°C., and preferably between about 20° and 32°C. Ordinarily, optimum production of the compound is obtained in about 2 to 10 days. The medium normally remains weakly acidic (pH 5.5 – 7.0) during the fermentation. The final pH is dependent, in part, on the buffers present, if any, and in part on the initial pH of the culture medium which is advantageously adjusted to about pH 7.0 prior to sterilization.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating this broth culture with an aliquot from a soil or a slant culture. When a young, active vegetative inoculum has thus been secured, it is transferred aseptically to large vessels or tanks. The medium in which the vegetative inoculum is produced can be the same as, or different from, that utilized for the production of the new compound, as long as it is such that a good growth of the microorganism is obtained.

The new antibiotic of the invention, U-43,795, is an amphoteric compound. It is soluble in $H_2O$ and slightly soluble in $CH_3OH$.

A variety of procedures can be employed in the isolation and purification of U-43,795, for example, absorption procedures followed by elution with a suitable solvent, column chromatography, partition chromatography, and crystallization from solvents.

In a preferred recovery process, U-43,795 and concurrently produced AT-125 are recovered from their culture medium by filtration through a medium porosity diatomite, for example FW 40 supplied by Eagle Picher. Other suitable diatomites are marketed under the trade names Super Cel (Johns Manville's fine diatomite), Dicalite 4200 (Great Lakes), and Miraflo 40 (Eagle Picher).

The clear beer is percolated through a chromatographic column packed with a styrene type sulfonic acid resin. Dowex 50 in the hydrogen form is preferred, advantageously highly crosslinked, for example Dowex 50 × 16. Other suitable resins are marketed under the tradenames Amberlite IR-120, Nalcite HCR, Chempro C-20, Permutit Q and Zeokarb 225. After appropriate washing of the column the antibiotic is eluted with a base, $NH_4OH$ is preferred. The antibiotically-active eluates obtained from the above chromatographic column are pooled and concentrated.

In a preferred purification procedure, the resulting aqueous concentrate, described above, at a neutral pH (6.2 – 7.8) is percolated through a column containing a weakly basic styrene type polyamine resin. Amberlite IR 45 ($OH^-$) is preferred. Other resins which can be used are Amberlite IR 4B, Nalcite WBR, DeAcidite E and Duolite A.2.

The column is washed with deionized water, 50% aqueous MeOH, and 90% aqueous MeOH, and then eluted with HOAc in 90% MeOH. Active eluate fractions are pooled, then evaporated to dryness under reduced pressure to give a residue. MeOH can be substituted by $H_2O$.

The residue, obtained as described above, containing both U-43,795 and AT-125, is then subjected to chromatographic separation using silica gel 60 (Number 7734 from E. Merck Darmstadt) and the solvent system methyl ethyl ketone:acetone:water in the proportions 65:20:15. This procedure affords relatively pure preparations of U-43,795 and AT-125.

The titer of AT-125 in the beer during various stages of recovery operations can be monitored by a disc-plate assay using *Bacillus subtilis* cultivated in a synthetic medium of the following composition:

| | |
|---|---|
| $Na_2HPO_4.7H_2O$ | 1.7 g. |
| $KH_2PO_4$ | 2.0 g. |
| $(NH_4)_2SO_4$ | 1.0 g. |
| $MgSO_4$ | 0.1 g. |
| Glucose | 2.0 g. |
| Bacto Agar* | 15.0 g. |
| Distilled water | 1 liter |
| Metallic ion stock solution** | 1 ml. |

*Bacto Agar provided by Difco Laboratories, Detroit, Michigan
**Metallic ion stock solution consists of the following:

| | |
|---|---|
| $NaMoO_4.2H_2O$ | 200 µg/ml. |
| $CoCl_2$ | 100 µg/ml. |
| $CuSO_4$ | 100 µg/ml. |
| $MnSO_4$ | 2 mg./ml. |
| $CaCl_2$ | 25 mg./ml. |
| $FeCl_3.4H_2O$ | 5 mg./ml. |
| $ZnCl_2$* | 5 mg./ml. |

*$ZnCl_2$ has to be dissolved separately using a drop of 0.1 N HCl for 10 ml. of water. The stock solution is heated to bring all the compounds in solution, kept standing for 24 hours, and sterile filtered.

This medium is inoculated with a spore suspension of *B. subtilis* ($1.5 \times 10^{10}$ cells/ml.) at a rate of 0.5 ml./liter. The beer samples are applied to 12.5 mm. diameter adsorbent paper discs (0.08 ml./disc), the assay system is incubated overnight at 37° C., and the zones of inhibition are measured. The potency of the sample is related to the diameter of the inhibition zone by means of the usual standard curve.

This medium when seeded with *B. subtilis* can also be used for the detection of antibiotic AT-125. U-43,795 can be detected by bioautography in relatively pure samples, i.e., samples free of antibiotic AT-125. In this procedure, papergrams are developed with the upper phase of a solvent mixture of 1-butanol, methanol, benzene, and $H_2O$ (2:1:1:1). After development the sheets are dried and the papergrams are then laid on transparent papergram trays containing the seeded medium and withdrawn after about 20 minutes. The trays are incubated overnight as above, and inhibition zones observed.

Since U-43,795 is an amphoteric compound, it forms salts with acids, alkali metals (including ammonia), alkaline earth metals (including magnesium and aluminum), and amines. Metal salts can be prepared by dissolving U-43,795 in water, and adding a dilute metal base until the pH of the solution is 7 to 8. U-43,795 metal salts include the sodium, potassium and calcium salts. Amine salts, including those with organic bases such as primary, secondary, and tertiary, mono-, di-, and polyamines can also be formed using the above-described or other commonly employed procedures. Further, ammonium salts can be made by well-known procedures. Other salts are obtained with therapeutically effective bases which impart additional therapeutic effects thereto. Such bases are, for example, the purine bases such as theophyllin, theobromin, caffein, or derivatives of such purine bases; antihistaminic bases which are capable of forming salts with weak acids; pyridine compounds such as nicotinic acid amide, isonicotinic acid hydrazide, and the like; phenylalkylamines such as adrenalin, ephedrin, and the like; choline, and others.

Acid salts can be made by neutralizing U-43,795 with the appropriate acid to below about pH 7.0, and advantageously to about pH 2 to pH 6. Suitable acids for this purpose include hydrochloric, sulfuric, phosphoric, sulfamic, hydrobromic, and the like. Acid and base salts of U-43,795 can be used for the same biological purposes as the parent compound.

U-43,795 is active against *Bacillus subtilis* and can be used in petroleum product storage to control this microorganism which is a known slime and corrosion producer in petroleum products storage. Still further, since U-43,795 is active against *Bacillus subtilis*, it can be used to minimize or prevent odor in fish or fish crates caused by this organism; or U-43,795 can be used to swab laboratory benches and equipment in a bacteriology laboratory contaminated with *Bacillus subtilis* and/or *Sarcina lutea*.

U-43,795 is active against L1210 murine leukemia in laboratory mice, and, thus, can be used to treat said mice.

U-43,795 can be acylated under standard acylating conditions with an appropriate acid halide or anhydride, or sulfonyl halide to give the corresponding bis acyl derivative wherein the 4-hydroxyl and α-amino hydrogen are acylated. The acylation is carried out in the presence of a weak acid-binding agent.

Suitable acid-binding agents include amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, terbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and lower alkoxyhydrocarbon carboxylic acids include hydrocarboncarboxylic acids as given above which are substituted by one or more of halogen, nitro, hydroxy, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are:
mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
and the like.

The acylation, advantageously, is conducted by treating a solution of U-43,795 in an acid anhydride with a small amount of base and heating the resulting mixture, if desired, for a short period at about 100° C. to complete the reaction. Water can be added to the reaction mixture to hydrolyze the acylating agent and the desired product can be isolated by conventional procedures. Further, the bis acyl derivative can be converted under standard esterification procedures as disclosed in Szmuszkovicz J. Org. Chem. 29, 843 (1964) to yield the corresponding bis acyl esterified derivative. The sequence of these reactions can be depicted as follows:

"Bis acyl" derivatives

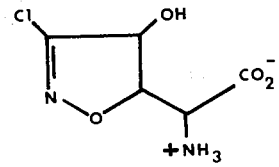

Standard acylating conditions with appropriate acid halide or anhydride, or sulfonyl halide

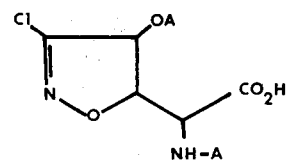

A = hydrocarbon carboxylic acid acyl of 2–18 carbon atoms, inclusive, halo-, nitro-, hydroxy-, amino-, cyano-, thiocyano-, and lower-alkoxy-substituted hydrocarbon carboxylic acid acyl of from 2 to 18 carbon atoms, inclusive, or, —SO₂R where R = CH₃ or

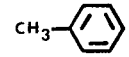

Conversion to mixed anhydride with EtO—CO—Cl or to acid chloride followed by reaction with appropriate alcohols or amines standard esterification procedures

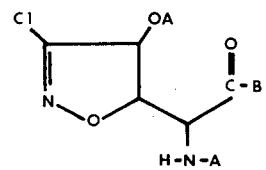

A as above
B = $\begin{Bmatrix} -N-R' \\ \phantom{-}H \\ -O-R' \end{Bmatrix}$ where R' = alkyl of 1–20 carbon atoms, inclusive, and isomeric forms thereof Examples of alkyl of from 1 to 20 carbon atoms, inclusive, and isomeric forms thereof, which are within the scope of the subject invention are as follows: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl, and the isomeric forms thereof.

Further, U-43,795 can be converted to aminoacyl nitrogen derivatives by standard reactions [See R. A. Boissonnas *Advances in Organic Chem.* 3, 159 (1963)] by first reacting the amino nitrogen with a suitable protective group, for example carbobenzyloxy (Cbz) chloride or carboethoxy phthalimide, or by utilizing selective acylating conditions with acyl anhydrides. The resulting compound can then be esterified using standard esterification procedures followed by hydrolysis of the amino nitrogen blocking group. The sequence of the above reactions can be depicted as follows:

"Monoacyl" nitrogen derivatives

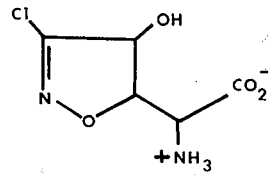

| carbobenzyloxy chloride or
| carboethoxy phthalimide or
| selective acylating conditions
▼ with acyl anhydrides

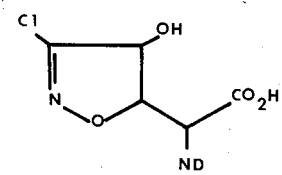

aqueous base

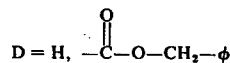

D = H, $-\overset{\overset{O}{\|}}{C}-O-CH_2-\phi$ or, 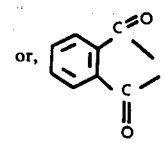

or, hydrocarbon carboxylic acid acyl of 2–18 carbon atoms, inclusive; halo-, nitro-, hydroxy-, amino-, cyano-, thiocyano-, and loweralkoxy-substituted hydrocarbon carboxylic acid acyl of from 2 to 18 carbon atoms, inclusive.

| standard esterification
▼ procedures (+ amide formation)

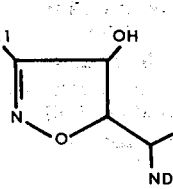

standard removal of Cbz or phthalimido blocking groups

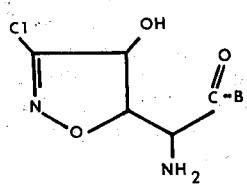

B = $\begin{matrix} -NR \\ \phantom{-}H \\ -OR \end{matrix}$ where R = alkyl of 1–20 carbon atoms, inclusive, and isomeric forms thereof
D as above Further, U-43,795 can be converted to monoacyl oxygen derivatives by first protecting the amino nitrogen, as disclosed above, and then acylating the protective group by standard acylating conditions, also as disclosed above. The amino blocking group can then be removed or the protected acylate can be esterified using standard esterification conditions as disclosed above, to yield the esterified amino acyl oxygen derivative. The sequence of the above reaction can be depicted as follows:

"Monoacyl" oxygen derivatives

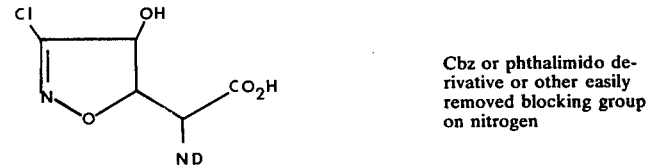

Cbz or phthalimido derivative or other easily removed blocking group on nitrogen

| standard acylating
| conditions

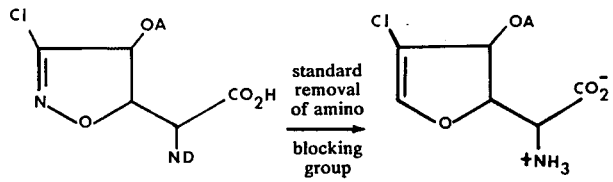

standard removal of amino blocking group

| standard esterification
| (+ amide forming)
| procedures

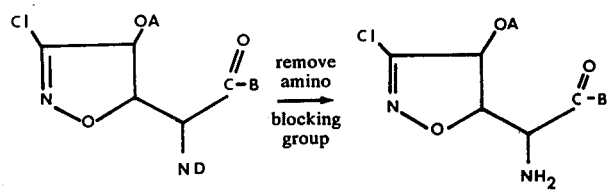

remove amino blocking group

The acyl and ester groups are as given above for the bis acyl derivatives of U-43,795.

The above derivatives of U-43,795 can be used for the same purposes as disclosed above for U-43,795.

The following examples are illustrative of the process and products of the invention, but are not to be construed as limiting. All percentages are by weight and all solvent mixture proportions are by volume unless otherwise noted.

EXAMPLE 1

A. Fermentation

A soil stock of *Streptomyces sviceus*, NRRL 5439, is used to inoculate 500-ml. Erlenmeyer seed flasks containing 100 ml. of sterile medium consisting of the following ingredients:

| | |
|---|---|
| Dextrose | 25 g./l. |
| Pharmamedia* | 25 g./l. |
| Tap water q.s. | to 1 liter |

*Product of Trader's Oil Mill Company, Fort Worth, Texas.

The seed medium presterilization pH is 7.2. The seed inoculum is grown for 2 days at 28° C. on a Gump rotary shaker operating at 250 r.p.m. Seed inoculum, prepared as described above, is used to inoculate 500-ml. Erlenmeyer fermentation flasks containing 100 ml. of sterile fermentation medium consisting of the following ingredients:

| | |
|---|---|
| NH₄Cl | 5 g./l. |
| Cerelose | 2 g./l. |
| Cornstarch | 10 g./l. |
| Washed yeast | 2.5 g./l. |
| KaySoy* | 20 g./l. |
| Lard oil | 1 ml. |
| Tap water q.s. | to 1 liter |

*Finely milled fat extracted soybean meal.

The presterilization pH is adjusted to 7.2 with 4 N NaOH. The fermentation flasks are inoculated at the rate of 5 ml. of seed inoculum per 100 ml. of fermentation medium. The fermentation flasks are grown for 2–3 days at a temperature of 32° C. on a Gump rotary shaker operating at 250 r.p.m.

B. Recovery

Whole beer (250 liters) from an AT-125 and U-43,795 fermentation as described above, is filtered through a medium porosity diatomite. The resulting clear beer is percolated at pH 7–8 through 25 liters of freshly regenerated Dowex 50 × 16 (H$^+$) in a chromatographic column. The column is washed with 50 liters of deionized H$_2$O and then eluted with 120 liters of 1 N NH$_4$OH; 6 liter fractions are collected. The most active fractions (inhibition zones >50 mm.) are determined by applying dipped, air-dried discs to a tray of *Bacillus subtilis* (grown in synthetic medium as described previously). The active fractions are pooled and concentrated under reduced pressure to remove excess NH$_4$OH.

C. Purification (1) Weakly basic styrene type polyamine resin column

The active aqueous concentrated Dowex 50 eluate, prepared as described above, at pH 7–7.5, is percolated through a column containing 4 liters of Amberlite IR 45 (OH$^-$). The column is washed with 8 liters of deionized H$_2$O, 4 liters of 50 percent aqueous MeOH and 8 liters of 90 percent aqueous MeOH, and then eluted with 0.5 N HOAc in 90 percent MeOH: 2 l. fractions are collected. The most active fractions by *Bacillus subtilis* assay, are pooled and evaporated to dryness under reduced pressure.

(2) Silica gel chromatography

The following procedure employs silica gel 60 (Number 7734 from E. Merck Darmstadt) and is carried out on the IR 45 (OH$^-$) residues obtained as described above. Active fractions (containing 6.55 gms., 934 BU/mg. or 5.84 percent AT-125) from an IR 45 column, as described above, are evaporated to dryness and the HOAc chased with water. The resulting residue is suspended in 328 ml. H$_2$O and evaporated onto 33 gms. of silica gel. The flask is rinsed with 5 gms. of fresh silica gel. Homogenous powder is chromatographed on a column of silica gel prepared by slurrying 600 gms. of silica gel in methyl ethyl ketone:acetone:water (65:20:15). The column is eluted with 7200 ml. of that solvent, initially collecting 1200 ml. (Number 0) and then cutting 500 ml. fractions (1–12). The results are as follows:

| No. | B.S.S. Zone[2] (1–10)[1] | 5λ Spotted on Silica Gel Plate Ninhydrin Detection | TLC[3] |
|---|---|---|---|
| 0 | 0 | | |
| 1 | 0 | No Zone | |
| 2 | 23H | No Zone | |
| 3 | 29 | Strong | U-43,795 |
| 4 | 30 | Strong | U-43,795 |
| 5 | 57 | Medium | U-43,795 + AT-125 |
| 6 | 70 | Medium | AT-125 |
| 7 | 70 | Medium/weak | AT-125 |
| 8 | 60 | Weak | AT-125 |
| 9 | 55 | Weak | |
| 10 | 47 | Weak | |
| 11 | 32 | Weak | |
| 12 | 0 | | |

[1]1–10 dilutions of fractions were spotted.
[2]B.S.S. Zone refers to the zone of inhibition (in mm.) on a B. subtilis disc plate assay as described above.
[3]Methyl ethyl ketone:acetone:water (65:20:15) on silica gel plate. Ninhydrin detection.

Fractions 3 and 4 are pooled and evaporated under reduced pressure at 40° C; the residue is triturated with MeOH affording 1.37 gm. of essentially pure U-43,795. Recrystallization from aqueous MeOH affords the analytically pure U-43,795 in the form of its crystalline hydrate. Water of hydration can be removed by drying.

Similarly, crystallization of fractions 6–8 afforded 0.37 gm. of essentially pure AT-125 which yielded analytically pure AT-125 on recrystallization from aqueous MeOH.

Salts of U-43,795 hydrate can be made as disclosed above for U-43,795 non-hydrate. U-43,795 hydrate and its salts can be used for the same purposes as U-43,795 nonhydrate, as disclosed above.

A biounit of activity (BU) is defined as that quantity of antibiotic necessary to achieve a 20 mm. zone of inhibition from a ½ inch disc treated with 0.08 ml. of its solution. The disc plate assay is as described previously.

We claim:
1. A composition of matter, essentially pure antibiotic U-43,795, which can be represented by the following structural formula:

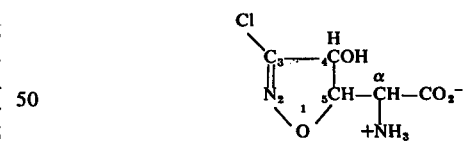

and its salts.

2. Acid addition salts of antibiotic U-43,795, the compound of claim 1.

3. Cationic salts of antibiotic U-43,795, the compound of claim 1.

4. Zwitterion form of antibiotic U-43,795, the compound of claim 1.

5. A composition of matter, essentially pure antibiotic U-43,795 hydrate, which can be represented by the following structural formula:

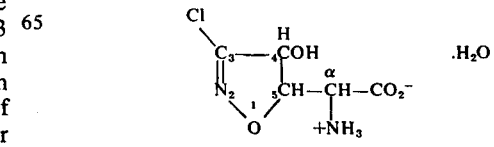

and its salts.

6. Acid addition salts of antibiotic U-43,795 hydrate, the compound of claim 5.

7. Cationic salts of antibiotic U-43,795 hydrate, the compound of claim 5.

8. Zwitterion form of antibiotic U-43,795 hydrate, the compound of claim 5.

* * * * *

UNITED STATES PATENT AND TRADEMARK OFFICE
CERTIFICATE OF CORRECTION

PATENT NO. : 3,944,562
DATED : March 16, 1976
INVENTOR(S) : David G. Martin and Ladislav J. Hanka It is certified that error appears in the above-identified patent and that said Letters Patent are hereby corrected as shown below:

Column 1, lines 20-22, in the formula, for  "$\overset{\alpha}{-\text{CH}-}$"    read -- $-\overset{\alpha}{\underset{\overset{+|}{\text{NH}_3}}{\text{CH}}}-$ --.
     $^+\text{NH}_3$ Column 2, lines 6-7, in the formula, for  "$\overset{\alpha}{-\text{CH}-}$"    read -- $-\overset{\alpha}{\underset{\overset{+|}{\text{NH}_3}}{\text{CH}}}-$ --.
     $^+\text{NH}_3$ Column 11, line 33, in the formula, for    read --  --.

Signed and Sealed this

Thirteenth Day of July 1976

[SEAL]

Attest:

RUTH C. MASON
Attesting Officer

C. MARSHALL DANN
Commissioner of Patents and Trademarks